(12) United States Patent
Lewis et al.

(10) Patent No.: US 6,926,740 B2
(45) Date of Patent: *Aug. 9, 2005

(54) MODULAR ORTHOPAEDIC IMPLANT APPARATUS AND METHOD

(75) Inventors: Paul P. Lewis, Warsaw, IN (US); James M. Kennedy, Berkley, MA (US); Phillip G. Withee, Taunton, MA (US)

(73) Assignee: DePuy Products, Inc., Warsaw, IN (US)

( * ) Notice: Subject to any disclaimer, the term of this patent is extended or adjusted under 35 U.S.C. 154(b) by 128 days.

This patent is subject to a terminal disclaimer.

(21) Appl. No.: 10/319,293

(22) Filed: Dec. 13, 2002

(65) Prior Publication Data

US 2004/0117029 A1 Jun. 17, 2004

(51) Int. Cl.$^7$ .................................................. A61F 2/32
(52) U.S. Cl. .................................................. 623/22.28
(58) Field of Search ........................... 623/11.11, 16.11, 623/18.11, 22.11, 22.22, 22.23, 22.24, 22.25, 22.28, 22.35, 22.4, 22.42, 23.11, 23.12, 23.13; 606/53, 86, 91

(56) References Cited

U.S. PATENT DOCUMENTS

| | | | |
|---|---|---|---|
| 4,624,674 A | | 11/1986 | Pappas et al. |
| 4,666,450 A | * | 5/1987 | Kenna .................... 623/22.28 |
| 4,960,427 A | | 10/1990 | Noiles |
| 5,002,577 A | | 3/1991 | Bolesky et al. |
| 5,156,626 A | | 10/1992 | Broderick et al. |
| 5,507,824 A | | 4/1996 | Lennox |
| 5,658,348 A | * | 8/1997 | Rohr, Jr. .................. 623/22.29 |
| 5,800,556 A | | 9/1998 | Sanders et al. |
| 5,879,399 A | * | 3/1999 | Church .................... 623/22.25 |
| 5,879,401 A | | 3/1999 | Besemer et al. |
| 5,888,208 A | | 3/1999 | Ro |
| 5,888,211 A | | 3/1999 | Sanders |
| 5,938,702 A | * | 8/1999 | Lopez et al. ............. 623/22.38 |
| 5,989,294 A | * | 11/1999 | Marlow .................... 623/22.16 |
| 6,013,104 A | | 1/2000 | Kamper |
| 6,152,961 A | * | 11/2000 | Ostiguy et al. .......... 623/22.28 |
| 6,162,256 A | * | 12/2000 | Ostiguy et al. .......... 623/22.26 |
| 6,193,759 B1 | | 2/2001 | Ro et al. |
| 6,312,470 B1 | | 11/2001 | Malawer |
| 6,340,370 B1 | | 1/2002 | Willert et al. |
| 6,352,559 B1 | | 3/2002 | Church |
| 6,416,553 B1 | | 7/2002 | White et al. |
| 6,475,243 B1 | * | 11/2002 | Sheldon et al. .......... 623/22.28 |
| 6,610,097 B2 | * | 8/2003 | Serbousek et al. ....... 623/22.24 |
| 6,682,566 B2 | * | 1/2004 | Draenert ................. 623/22.24 |
| 2004/0078083 A1 | * | 4/2004 | Gibbs et al. ............. 623/22.14 |

FOREIGN PATENT DOCUMENTS

| | | |
|---|---|---|
| DE | 100 36 987 | 2/2002 |
| EP | 0 612 509 | 8/1994 |
| EP | 0 974 316 | 1/2000 |

* cited by examiner

*Primary Examiner*—Kevin Shaver
*Assistant Examiner*—Anuradha Ramana
(74) *Attorney, Agent, or Firm*—Maginot, Moore & Beck

(57) ABSTRACT

A trial implant kit includes a plurality of intermediate components and a plurality of inner components. Each of the plurality of intermediate components has a uniform inner surface, although at least two of the plurality of intermediate components having distinct outer surfaces. Each of the distinct outer surfaces is configured to engage one of a plurality of acetabular shell component geometries. Each of the plurality of inner components has a uniform outer surface portion and a bearing surface, the uniform outer surface portion configured to be received by the uniform inner surface of any of plurality of intermediate components. The bearing surface is configured to engage a femoral head. At least two of plurality of inner components having distinct bearing surface configurations.

14 Claims, 9 Drawing Sheets

MODULAR ORTHOPAEDIC IMPLANT APPARATUS AND METHOD

FIELD OF THE INVENTION

The present invention relates generally to prosthetic orthopaedic implants, and more particularly, to methods and apparatus for implanting modular orthopaedic implants.

BACKGROUND OF THE INVENTION

Many orthopaedic procedures involve the implantation of prosthetic devices to replace badly damaged or diseased bone tissue. Common orthopaedic procedures that involve prosthetic devices include total or partial hip, knee and shoulder replacement. For example, a hip replacement often involves a prosthetic femoral implant. The femoral implant usually includes a rigid stem that is secured within the natural femur bone tissue. The femoral implant further includes a rounded head that is received by, and may pivot within, a natural or artificial hip socket. Knee replacement is somewhat similar, and typically includes one or more implants that have both bearing surfaces and stems.

Total hip replacement procedures typically involve the implantation of two main component systems: the femoral component (as discussed above) and an acetabular component. The femoral component is anchored within the existing femur and includes a head that replaces the natural hip joint femoral head. The acetabular component is secured within the acetabulum of the patient and serves as a bearing surface for the femoral component.

Many acetabular cups include an outer shell component and an inner liner. The outer shell component has an outer dimension configured to fit within the acetabulum of the patient. The outer shell is typically formed from a high strength alloy, such as a titanium alloy, in order to withstand the pressures exerted on the hip joint during normal activities. The inner liner is configured to tightly fit within the acetabular outer shell component. The inner liner serves as the bearing surface for the femoral head. Accordingly, the inner liner is typically constructed of a polymeric material, such as for example, polyethylene. Inner liners may also be constructed of cobalt chrome or ceramic material.

The acetabular component of hip replacement includes a number of sizing and shape considerations. In particular, the outer diameter of the outer shell is configured to be received by the patient's acetabulum. While the acetabulum may be reamed and otherwise prepared to receive the outer shell, it is still necessary to provide multiple sizes of outer shells to accommodate the varied anatomies of different patients. In addition to the outer diameter of the outer shell, the inner diameter/geometry of the inner liner must be configured to receive the femoral head (prosthetic or otherwise) and allow a suitable range of motion. The inner diameter and geometry of the inner liner can often define 10–15 different styles.

Typically, the ultimate determination of which outer shells size and which inner liner style to use occurs during surgery. In particular, the surgeon usually first performs a trialing procedure in which one or more prosthetic devices are temporarily implanted. The trial devices are evaluated and then the final prosthetic device(s) is selected based on the evaluation of the trial devices.

During the trialing process, the surgeon assesses the acetabulum and the femoral head and attempts to select the correct combination of outer shell size and inner liner style. The outer shell is typically selected based on the geometry of the acetabulum identified by the surgeon. An inner liner must thereafter be selected. The inner liners are available in different sizes and styles. As discussed above, the size of the inner liner ultimately depends on the size of the femoral head. Different liner styles depend on patient geometry and can affect the range of motion. Examples of known liner styles include neutral, 10°, lateralized, and lipped. Each is appropriate for a particular situation.

Accordingly, in order to select the appropriate components for the acetabular implant, the surgeon implants trial components on a trial and error basis until a suitable combination of outer shell size and inner liner style provides acceptable results. To this end, surgeons must have available to them outer shells of various sizes and corresponding trial inner components of different styles and sizes. Moreover, in order to provide maximum flexibility, all possible styles and sizes of inner liners should be available for every possible size of outer shell component.

It can be readily be appreciated that providing inner liners having all of the possible configurations for each of the different size outer shell components can require a large number of trial components. For example, if there are six outer shell sizes and thirteen inner liner configurations, then up to seventy-eight inner liner trial components must be provided to the surgeon, thirteen styles for each of six outer shell sizes. Providing such a quantity of inner liner trial components in addition to six outer shell sizes is both costly and inconvenient to manipulate in the surgical environment.

One prior art patent, U.S. Pat. No. 5,879,401 to Besemer et al., which is incorporated herein by reference, teaches an acetabular trial system that in theory can reduce the number of trial liner components that are necessary to cover various outer shell sizes and inner liner styles. To this end, U.S. Pat. No. 5,879,401 teaches the use of outer shell components that have uniform inner diameters. Because the inner diameter of the outer shell is uniform regardless of its outer diameter, only one set of inner liners is necessary.

One drawback of such a design is that it requires the outer shells to have widely varying thicknesses. In particular, because the inner diameter of the outer shell remains the same while the outer diameter varies, the outer shell thickness must vary accordingly. In the case of the largest diameter outer shell, the thickness of the outer shell could well approach 16–20 mm in thickness. While such a design is possible, it has a number of drawbacks. One drawback relates to the use of final outer shell components in the trial reductions of the joint.

More specifically, because the outer shell may typically be selected prior to the trial reduction of the joint, surgeons often elect to implant the final outer shell, and not the trial outer shell, prior to performing the trial reduction using the trial inner liner. To permit the flexibility of using either final outer shell or the trial outer shell during trial reduction, the trial outer shell and the final outer shell must be substantially identical in dimensions. Moreover, if this flexibility is to be provided using the method of U.S. Pat. No. 5,879,401, then the final outer shell must, like the trial outer shell, be available in varying thicknesses in order to maintain the constant inner diameter. Thus, in the case of the largest outer shell sizes, the final outer shell can also require a thickness approaching 20 mm. However, normal outer shells have a thickness of on the order of 5 mm–8 mm.

It is undesirable to have such thick outer shells because thick outer shells require the use of correspondingly thinner inner bearing or liner devices. Thinner bearings or liners are undesirable because joint longevity increases as a function of liner thickness. In particular, because the liner serves as the bearing surface for the humeral head, a thicker liner will provide a bearing surface that can withstand greater wear. As a consequence, it is desirable to provide the final liner with larger thickness. Thus, if excess thickness is used for the outer shell, that excess thickness represents thickness that could have been used to increase the liner thickness and thus the longevity of the joint.

Thus, there are a number of drawbacks to varying the thickness of the outer shell component to accommodate various inner liner trials.

Accordingly, there is a need for a modular acetabular trial system and method that provides flexibility of outer shell sizes and inner liner styles with a reduced number of components, and which optionally allow the surgeon to employ final outer shell components during the trial reduction.

SUMMARY OF THE PRESENT INVENTION

The present invention addresses the above needs, as well as others, by providing a trial acetabular kit and associated method that employs a plurality of intermediate spacers configured to be received into the outer shell component. The intermediate spacers have a uniform inner diameter, but an outer diameter that corresponds to one of a plurality of outer shell sizes. The intermediate component allows for a single set of inner liners to be used with each of a plurality of sizes of outer shell components. Moreover, the intermediate spacers allow the outer shell to have a desired thickness that does not vary widely from size to size. In this manner, the trial outer shells may readily have the same dimensions as the final outer shell.

A first embodiment of the invention is a trial implant kit that includes a plurality of intermediate components and a plurality of inner components. Each of the plurality of intermediate components has a uniform inner surface, although at least two of the plurality of intermediate components having distinct outer surfaces. Each of the distinct outer surfaces is configured to engage one of a plurality of acetabular shell component geometries. Each of the plurality of inner components has a uniform outer surface portion and a bearing surface, the uniform outer surface portion configured to be received by the uniform inner surface of any of plurality of intermediate components. The bearing surface is configured to engage a femoral head. At least two of plurality of inner components having distinct bearing surface configurations.

Preferably, but not necessarily, the trial kit further includes a plurality of acetabular outer shell components.

A second embodiment of the invention is a method of implanting an acetabular component that includes disposing an intermediate component within an acetabular shell component, the intermediate component defining a cavity having a first average diameter; The method further includes disposing a first inner component within the intermediate component, the first inner component having a first of a plurality of bearing surface configurations, the first inner component configured to be received in the cavity of the intermediate component.

The advantages of the present invention may suitably have application in other orthopaedic implant devices. In particular, the use of an intermediate liner having a uniform inner geometry to act as an interface between various outer pieces and various inner pieces could have application in knee replacement, among others.

The above described features and advantages, as well as others, will become more readily apparent to those of ordinary skill in the art by reference to the following detailed description and accompanying drawings.

DETAILED DESCRIPTION

Figure 1:
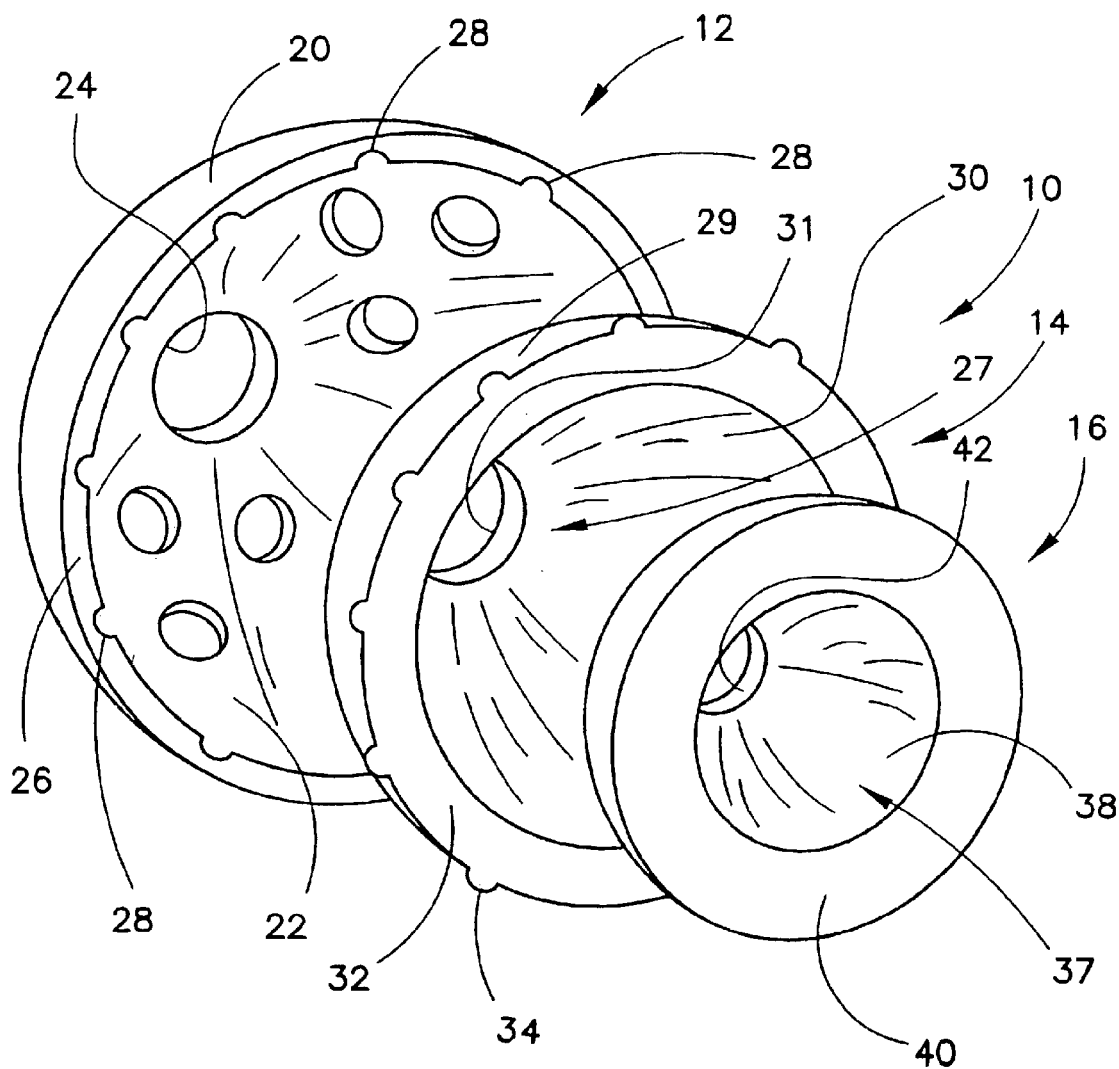
FIG. 1 shows a perspective exploded view of a modular trial acetabular assembly according to the present invention.

FIG. 1 shows an exploded perspective view of an exemplary modular acetabular trial 10 according to the present invention. The modular acetabular trial 10 is generally configured to be received in the acetabulum of a patient. The modular acetabular trial 10 is further configured to receive a femoral head, not shown, but which would be known in the art.

The components of the modular acetabular trial 10 are used, in whole or in part, as trial implants to ascertain the appropriate size and style of acetabular cup that will be finally implanted. In particular, the surgeon may use the components of the modular acetabular trial 10, either as a unit or as subcombinations, to determine the outer shell diameter and the inner liner style of the final acetabular cup implant.

The modular acetabular trial 10 includes an outer shell 12, an intermediate component 14 and an inner liner component 16. The outer shell 12 includes a rounded outer surface 20, which is substantially hemispherical, but may vary from a true hemisphere, depending on the application. The outer surface 20 interfaces with and secures to the acetabulum of a patient. The average diameter of the outer shell 20 will typically range from on the order of 68 mm to 80 mm, depending on the anatomy of the patient. The outer shell 12 further includes an inner surface 22 that has a shape substantially similar to the outer surface 20, although with a smaller diameter. In most embodiments, the inner surface 22 has a diameter that is 10 mm to 16 mm smaller than that of the outer surface 20. As a consequence, the outer shell 12 has a thickness of about 5 mm to 8 mm.

The outer shell 12 is typically contructed of stainless steel for use in trial applications. However, as will be discussed below, a trial outer shell need not always be used. In particular, a surgeon may elect to implant the final outer shell if the proper size of the outer surface may be determined without a trial implant. If the outer shell 12 is the final implant, the outer shell 12 will be constructed of a higher hardness alloy, such as a titanium alloy. For example, the outer shell 12 may be constructed of Ti-6Al-4V.

The outer shell 12 further includes a threaded bore 24 for receiving a threaded fastener, not shown, that secures the intermediate component 14 to the outer shell 12. (See also FIGS. 3 and 4). A substantially circular rim 26 is defined at the substantially circular edges of the outer surface 20 and the inner surface 22. The substantially circular rim 26 includes a plurality of small, substantial semi-circular depressions 28 that function as receptacles for complimentary features on the intermediate component 14, discussed further below.

Referring now to the intermediate component 14, the intermediate component 14 is in the form of a substantially hemispherical shell defining a cavity 27. The intermediate component 14 includes an outer surface 29, an inner surface 30, and a substantially circular rim 32. The outer surface 29 has a size and shape adapted to be received by the outer shell 12. In particular, the outer surface 29 of the intermediate component 14 is approximately the same size and shape as the inner surface 22 of the outer shell 12. The average diameter of the outer surface 29 is thus dictated by the size of the inner surface 22 of the outer shell 12. As a consequence, because the outer shell 12 can vary in diameter by about 12 mm to accommodate the anatomies of different patients, the diameter of the outer surface 29 of the intermediate component 14 will likewise vary by about 12 mm. For example, the outer surface 29 may suitably vary in size from about 52 mm to about 64 mm.

The inner surface 30 has a generally hemispherical shape that defines the shape of the cavity 27. The inner surface 30 has an average diameter that is less than that of the outer surface 29. Moreover, the inner surface 30 has an average diameter that is uniform for of the sizes of the intermediate component 14. In other words, regardless of the size of the intermediate component 14, the average diameter of the inner component 30 remains the same. As a consequence, if the diameter of the outer surface 29 is increased, then the thickness of the intermediate component 14 increases.

The diameter of the inner surface 30 is preferably, but not necessarily, chosen such that the thickness of the smallest intermediate component 14 is about 2–5 mm. Such thickness generally ensures the reliability of the component for use during the trial reduction. In the exemplary embodiment described herein, the intermediate component 14 is constructed from acetal, which is available as Delrin™ from 3M Co.

The rim 32 further includes a plurality of substantially semi-circular protrusions 34 that extend outward from the edge in which the outer surface 28 intersects with the edge 32. The protrusions 34 are configured to be received by the depressions 28 in the rim. When the intermediate portion 14 is seated within the outer shell 12, the protrusions 34 are received into the depressions and help inhibit rotational movement of the intermediate portion 14 with respect to the outer shell 12. The intermediate component 14 further includes a bore 31 that is configured to align with the threaded bore 24 of the outer shell 12.

The inner component 16 is a rounded component having an interior cavity 37 that includes an outer surface, not visible in FIG. 1, an inner bearing surface 38, and a substantially circular rim 40. At least a portion of the outer surface has a size and shape adapted to be received by the cavity 27 defined in the intermediate component 14. As will become apparent in the discussion of FIG. 4, a portion of the outer surface of the inner component 16 extends out of the cavity 27 and helps define an interface to the femoral head. The interface is also defined by the circular rim 40 and the inner bearing surface 38. To this end, the inner surface 38 defines an interior cavity 37, which is configured to receive one of a plurality of femoral heads, not shown.

More specifically, the inner bearing surface 38, has a plurality of configurations, each adapted to receive one of a plurality of femoral heads, and further adapted to include other shape features that affect the alignment and/or range of motion of the femoral head. Further detail regarding these features is provided below in connection with FIG. 2.

Regardless of the configuration of the bearing surface 38 of the inner component 16, the portion of the outer surface of the inner component 16 that is disposed within the inner surface 30 of the intermediate component 14 will have substantially a uniform average diameter. In particular, the average diameter of the outer surface of the inner component 16 will be substantially the same as the average diameter of the inner surface 30 of the intermediate component 14. As a consequence, both the inner surface 30 of the intermediate component 14 and the outer surface of the inner component 16 always fit together, regardless of which configurations of intermediate component 14 and inner component 16 are chosen.

As discussed above, the inner bearing surface 38 is selected to have a configuration that is suitable for the anatomy of the patient. The configuration of the inner bearing surface is defined by its size (average diameter) and style (shape/alignment).

In particular, the inner bearing surface 38 will have one of a plurality of sizes as measured by its average diameter. Preferably, the average diameters range from about 22 mm to about 36 mm. Because the outer diameter of the inner component 16 is constant and the inner diameter varies, the thickness of the inner component 16 will vary substantially, for example, from about 3 mm to about 10 mm.

In addition, the inner bearing surface 38 will have one a plurality of liner styles. For example, as is known in the art, inner liners of acetabular cups such as the inner component 16 may have a neutral bearing surface, a 10° bearing surface, a lipped bearing surface, or a laterized liner bearing surface. The inner bearing surface 38 shown in FIG. 1 is a standard neutral bearing surface. Selection among the various liner styles will depend on the anatomy of the patient, and is typically finally determined during trial reduction.

In the exemplary embodiment described herein, the inner component 16, like the intermediate component 14, is constructed from acetal, which is available as Delrin™ from 3M Co.

Figure 2:
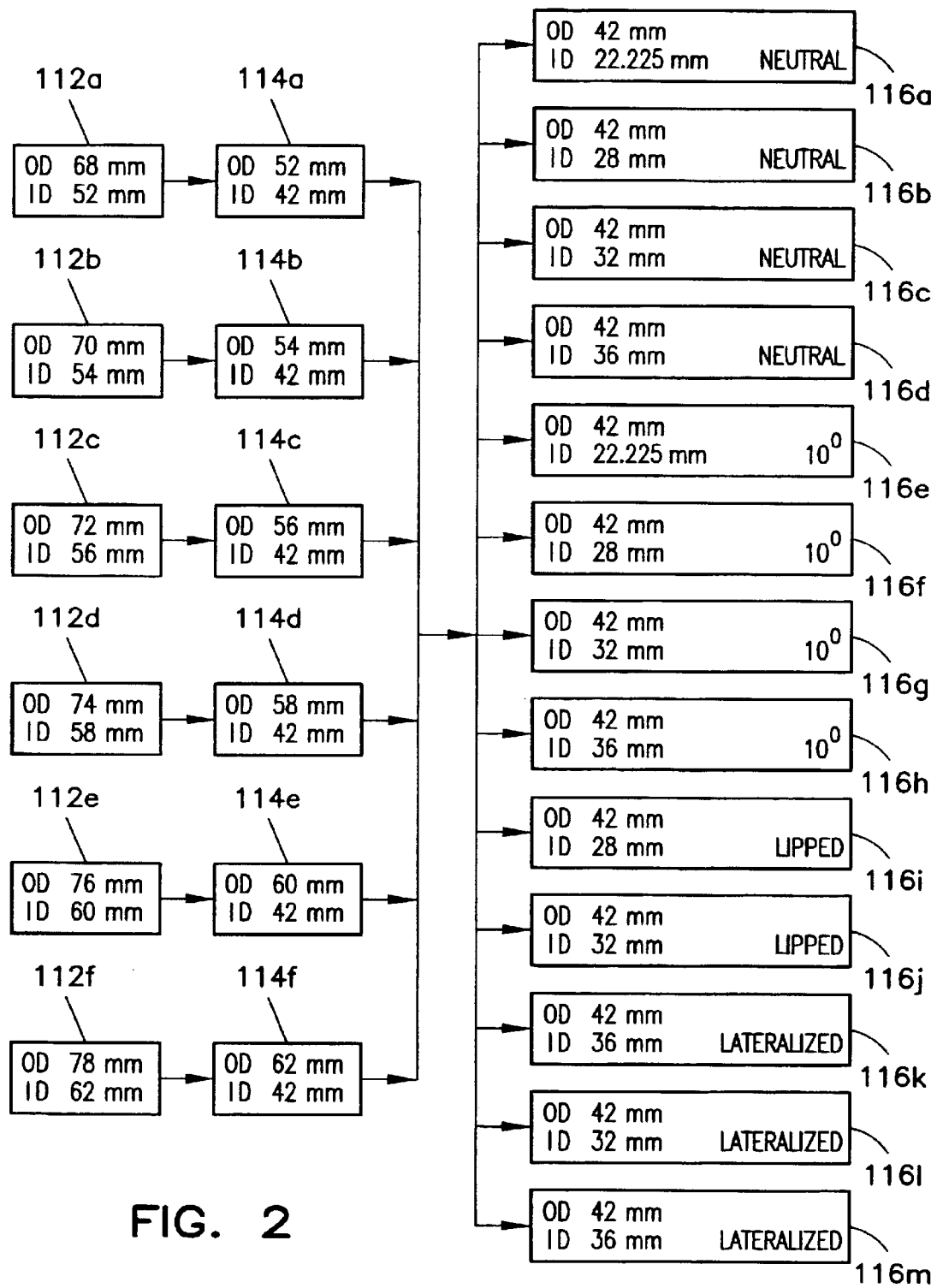
FIG. 2 shows an exemplary kit generated in accordance with the present invention.

FIG. 2 shows in schematic form an exemplary modular acetabular trial kit 100 in accordance with the present invention. The modular acetabular kit 100 of FIG. 2 includes a plurality of outer shells 112a–112f, a plurality of intermediate components 114a–114f, and a plurality of inner components or liners 116a–116m. The plurality of outer shells 112a–112f may suitably have the general shape of the outer shell 12 of FIG. 1. However, outer shells of other types that are typically employed in two-piece acetabular cups may be used. Regardless of the exact shape, each of the outer shells 112a–112f is defined by a specific combination of an outer diameter ("OD") and an inner diameter ("ID"). The OD varies so that the kit may accommodate differences in acetabulum size in patients. The ID varies more or less as a function of the OD in order to maintain a relatively consistent thickness of the outer shells 112a–112f.

The plurality of intermediate components 114a–114f may suitably have the general shape of the intermediate component 14 of FIG. 1. Regardless of the exact shape, each of the intermediate components 114a–114f has a specific combination of an OD and an ID. However, unlike the outer shells 112a–112f, the IDs of the intermediate components 114a–114f are uniform in size. Nevertheless, the ODs of the intermediate components 114a–114f vary such that each of the intermediate components 114a–114f has an OD that is substantially the same as the ID of one of the plurality of outer shells 112a–112f. Because the ODs of the intermediate components 114a–14f vary and the IDs are uniform, the thickness (defined as the OD–ID) is different for each of the intermediate components 114a–114f.

The plurality of inner components 116a–116m have the general shape of the inner component 16 of FIG. 1, but essentially include an outer surface portion having an OD and an inner bearing surface having one of a plurality of configurations defined by an ID and a liner style. The IDs of the inner components 116a–116m range from about 22 mm to 36 mm, and the liner styles include neutral, 10° lipped, and lateralized. In the exemplary embodiment described herein, thirteen configurations, each including a unique combination of ID and liner style, are available. A short description of the various styles follows, although details regarding the inner liner styles would be known to those of ordinary skill in the art.

Figure 3A:
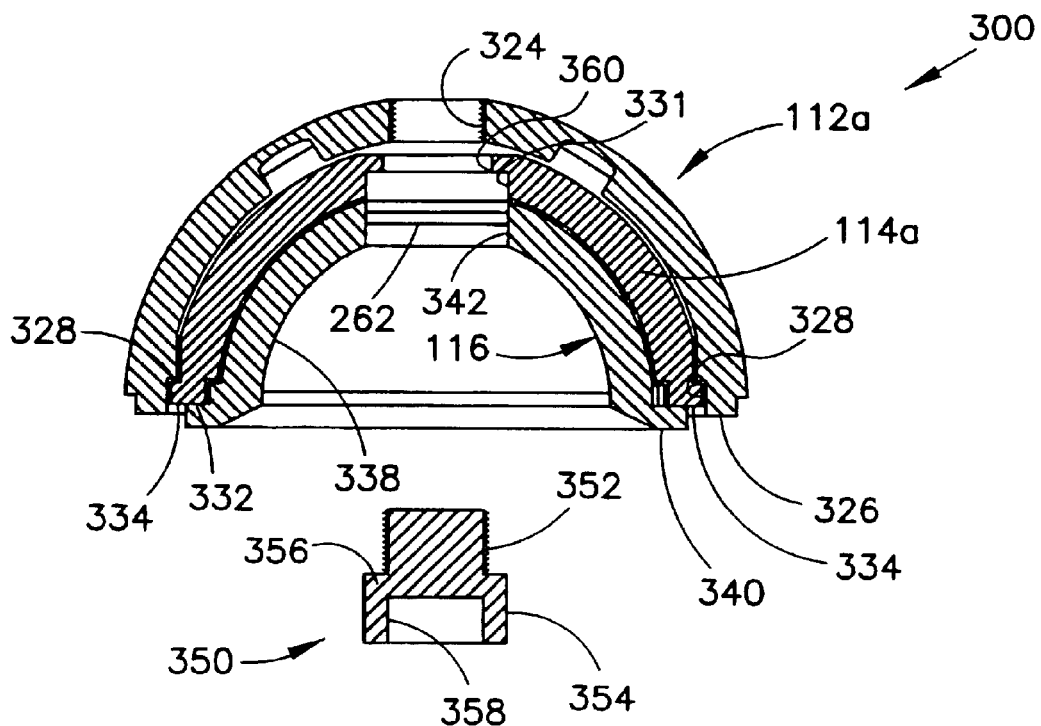
FIGS. 3a, 3b and 3c show a first exemplary modular trial acetabular assembly according to the present invention.

The neutral liner style (e.g. inner components 116a–116d) has a neutral bearing surface, exemplified by the inner bearing surface 338 of FIG. 3a. The neutral liner style is concentrically aligned with the outer shell and is indicated in normal circumstances.

Figure 4A:
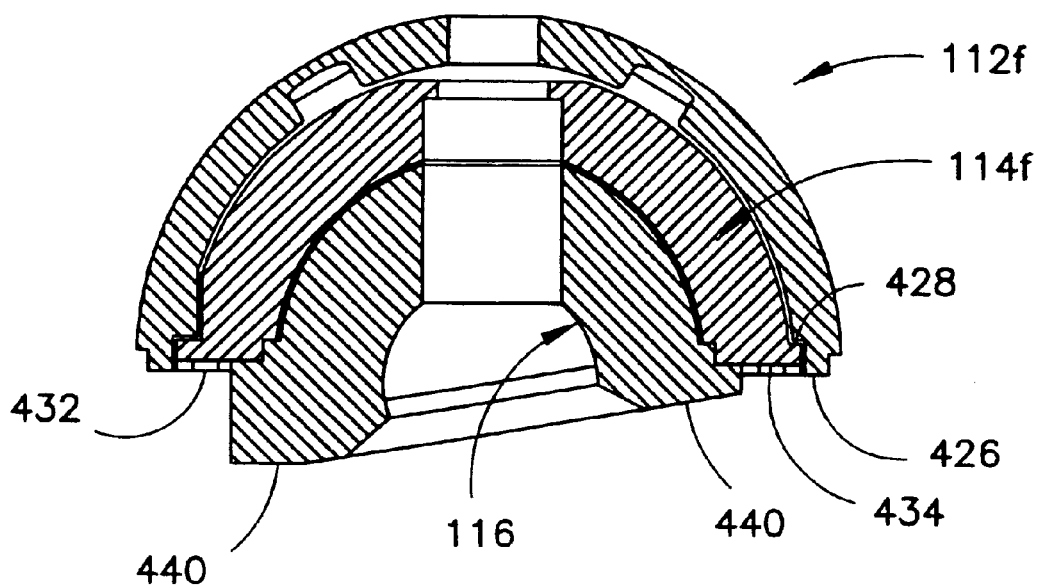
FIGS. 4a, 4b and 4c show a second exemplary modular trial acetabular assembly according to the present invention.

The 10° liner style (e.g. inner components 116e–116h) has an 10° offset bearing surface, exemplified by the inner bearing surface 438 of FIG. 4a. The 10° liner style provides a bearing surface that has an offset angle to the outer shell. The 10° liner style is used to correct anteversion in the leg, and may be required if the outer shell is implanted at an incorrect angle.

The lipped liner style (e.g. inner components 116i–116j) resembles the neutral liner style, except that one side of the liner extends out of the outer shell, forming a lip. The lipped liner style may be indicated if separation of the femoral head from the acetabular cup is observed during trial reduction.

The lateralized liner style resembles the neutral liner style except that the inner bearing surface is eccentric, or offset laterally with respect to the outer shell. The lateralized liner style may be indicated if soft tissue laxity is present or if extra-articular impingement is observed during trial reduction.

Referring again specifically to FIG. 2, the OD of each of the inner components 116a–116m is uniform, and is substantially the same as the ID of each of the intermediate components. In the exemplary embodiment described herein the OD of each of the inner components 116a–116m is 42 mm. As discussed above, because the ODs of the inner components 116a–116m are uniform and the IDs vary, the thickness of the inner components 116a–116m vary.

As shown in FIG. 2, the acetabular trial kit allows any of the outer shells 112a–112f to be mated with any of the inner components 116a–116m. The intermediate components 114a–114f provide an interface between the outer shells 112a–112f and the inner components 116a–116m to eliminate the need for thirteen different types of inner components for each of the six outer component sizes. Moreover, the outer shells 112a–112f, which can be made of a titanium alloy or stainless steel, are of relatively consistent thickness. As a consequence, a trial reduction may be performed using one or more of the inner components 116a–116m even if the final acetabular outer shell is employed instead of the trial outer shell.

FIGS. 3a–3c and FIGS. 4a–4c show two different exemplary acetabular trials 300 and 400 that may be formed from the kit 100 of FIG. 2. The acetabular trial 300 of FIGS. 3a, 3b and 3c includes an outer shell 112a from the kit 100 of FIG. 2 having an OD of 68 mm and an inner component 116d having a 36 mm ID and a neutral liner style. The acetabular trial 400 of FIGS. 4a, 4b and 4c includes an outer shell 112f from the kit 100 of FIG. 2 having an OD of 78 mm and an inner component 116e having a 22.225 mm and a 10° liner style.

Figure 3B:
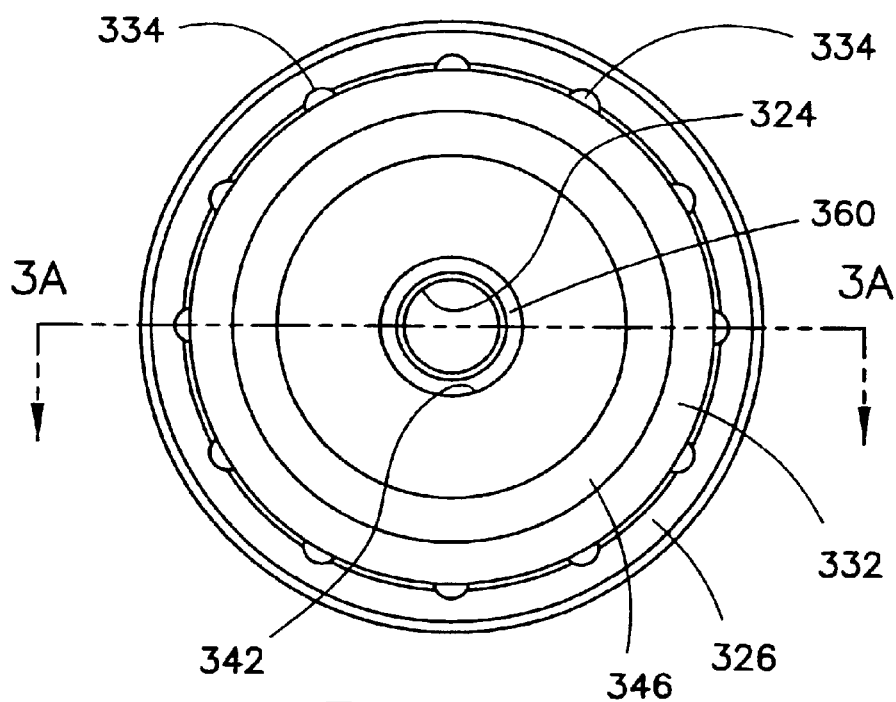
Figure 3C:
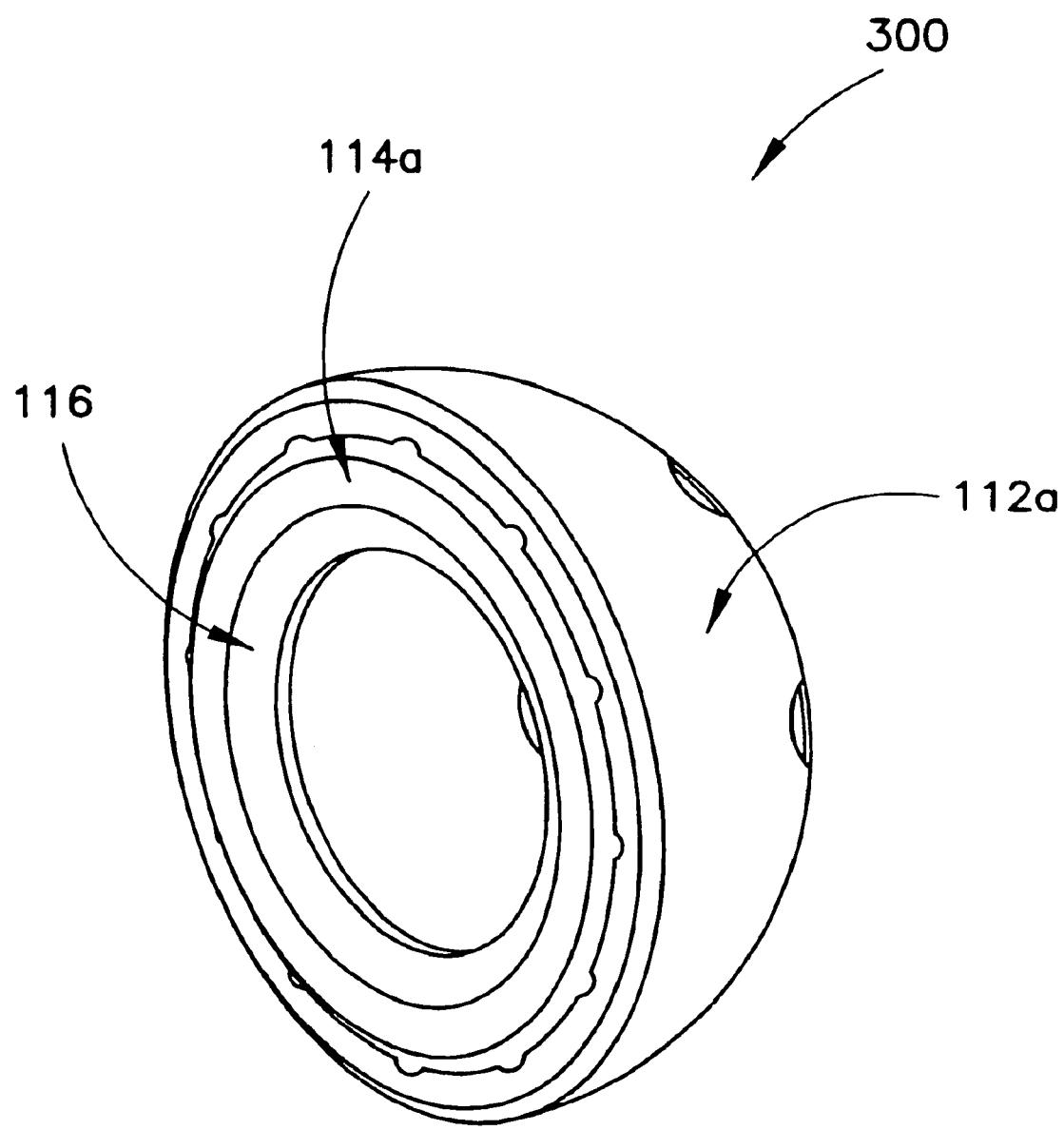

Referring more specifically to the acetabular trial 300 of FIGS. 3a, 3b, 3c, the inner component 116d is disposed within the intermediate component 114a, which in turn is disposed within the outer shell 112a. The intermediate component 114a has an OD of 52 mm, which corresponds to the ID of the outer shell 112a. The intermediate component 114a further has an ID of 42 mm, which is the uniform ID of the intermediate components 114a–114f of the kit 100. (See FIG. 2).

The intermediate component 114a includes protrusions 334 that nest within corresponding depressions 328 in a rim 326 of the outer shell 112a. The protrusions 334 and the depressions 328 cooperate to inhibit rotation of the intermediate component 114a with respect to the outer shell 112a.

The inner bearing surface 338 of the inner component 116d is in the neutral style. In the neutral style of the acetabular trial 300, the rim 340 of the inner component 116d, the rim 332 of the intermediate component 114a and the rim 326 of the outer component 112a all lay in substantially parallel planes. As such, the style is "neutral", meaning that there is no angle of inclination similar to that of the rim of the inner component 116e shown in FIG. 4 and discussed below.

The components 112a, 114a and 116d are assembled and secured together using a threaded fastener 350. The threaded fastener 350 includes a threaded end 352 that is received by the threaded bore 324 in the outer shell 112a. The threaded fastener 350 further includes a head 354 defined by an annular shoulder 356 and a hollow cylinder 358 extending upward therefrom. The annular shoulder 356 is configured to engage an annular ridge 360 in the bore 331 of the intermediate component 114a. The hollow cylinder 358 is configured to engage an annular detent 362 in the bore 342 of the inner component 116d in a friction fit.

It can be readily appreciated that any of the inner components 116a–116m can be used with the combination of the outer shell 112a and the intermediate component 114a. Thus, if during a trial reduction it is learned that the inner component 116d does not provide an adequate fit or alignment, another of the inner components 116a–116m may be substituted for the inner component 116d.

Figure 4B:
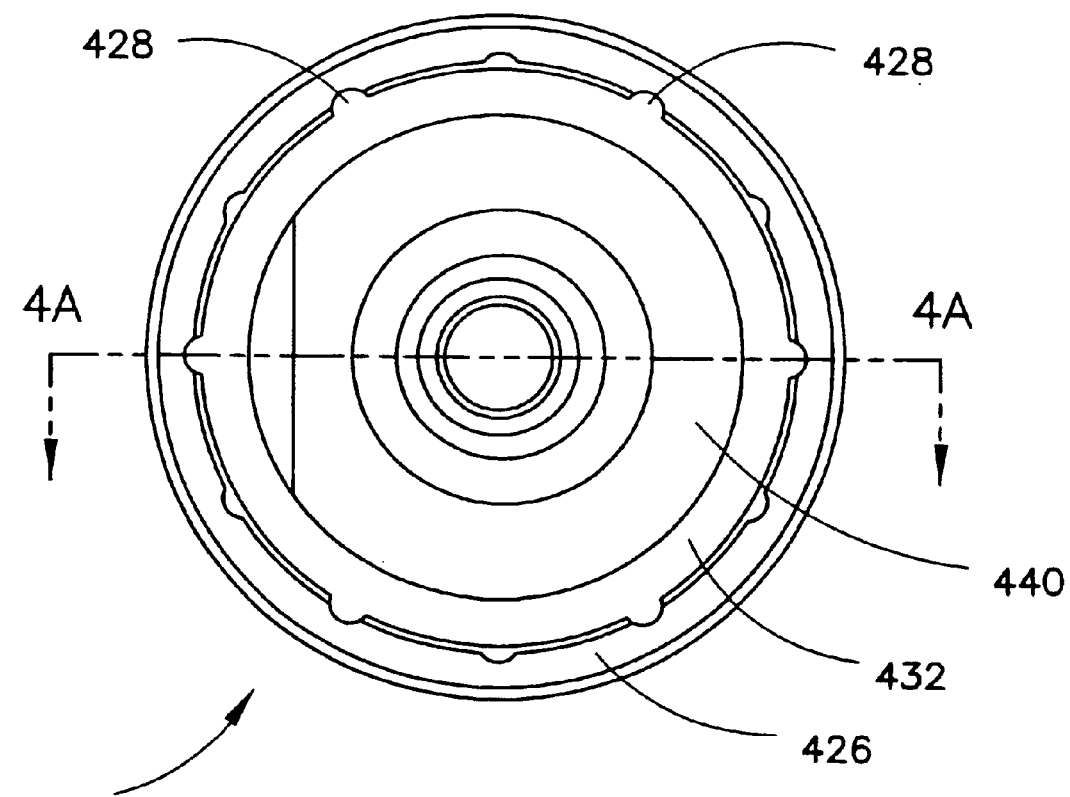
Figure 4C:
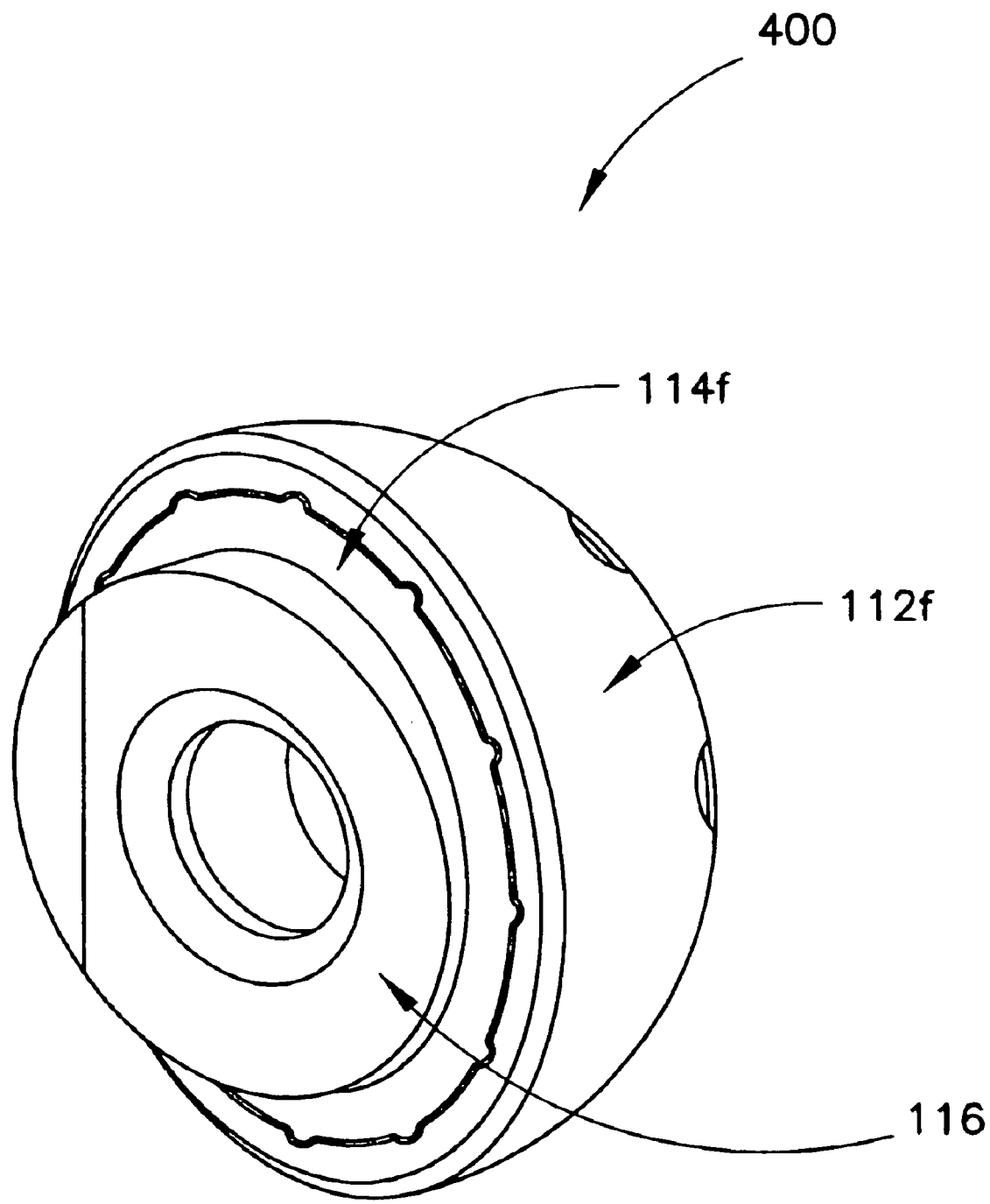

Referring specifically to the acetabular trial 400 of FIGS. 4a, 4b and 4c, the inner component 116e is disposed within the intermediate component 114f, which in turn is disposed within the outer shell 112f. The intermediate component 114f has an OD of 62 mm, which corresponds to the ID of the outer shell 112f. The intermediate component 114f further has an ID of 42 mm, which is the uniform ID of the intermediate components 114a–114f of the kit 100. (See FIG. 2).

Apart from the difference in thickness and OD, the intermediate component 114f is substantially structurally the same as the intermediate component 114a of FIG. 3. Specifically, the intermediate component 114f includes protrusions 434 that nest within corresponding depressions 428 in a rim 426 of the outer shell 112f. The protrusions 434 and the depressions 428 cooperate to inhibit rotation of the intermediate component 114f with respect to the outer shell 112f.

The inner bearing surface 438 has a 10° phase change style. In the 10° phase change style of the acetabular trial 400, the rim 440 of the inner component 116e is in a plane that is inclined with respect to the parallel planes in which the rim 432 of the intermediate component 114f and the rim 426 of the outer component 112f lie. As such, the style is not neutral, but inclined by 10°.

The components 112f, 114f and 116e are assembled and secured together using a threaded fastener, not shown, in an analogous manner as that described above in connection with FIG. 3.

The exemplary acetabular trials 300 and 400 thus illustrate the flexibility of the kit 100. The acetabular trial 300 has a relatively large ID defined by its inner component 116d and a relatively small OD defined by its outer shell 112a, while the acetabular trial 400 has a relatively small ID and a relatively large OD. The trials 300 and 400 also illustrate how different styles (neutral, 10° lipped, and lateralized) may be used. Those of ordinary skill in the art could readily incorporate these and other styles into inner bearing components as desired.

Figure 5A:
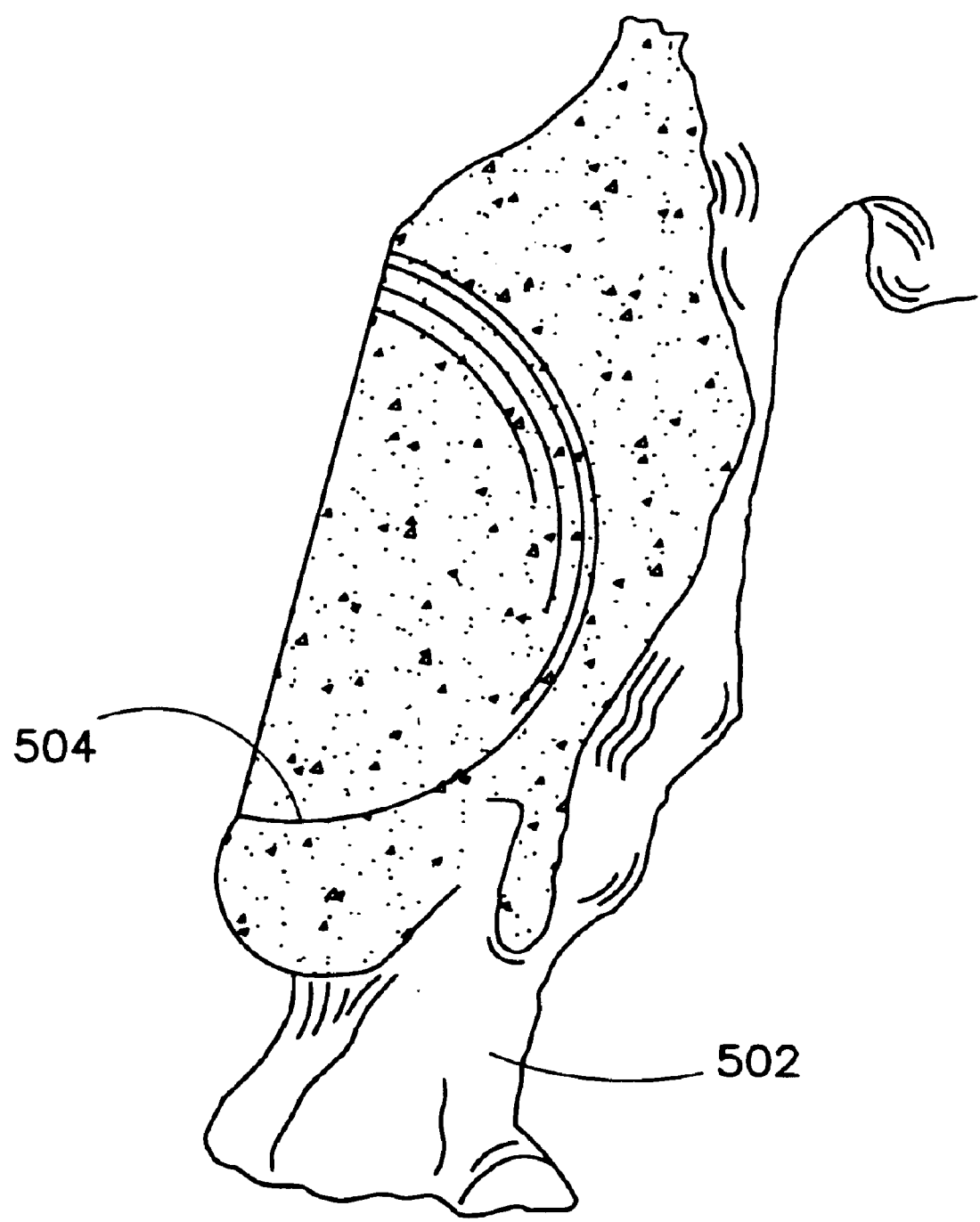
FIGS. 5a, 5b and 5c show a method of implanting an exemplary modular trial acetabular assembly according to the present invention.
Figure 5B:
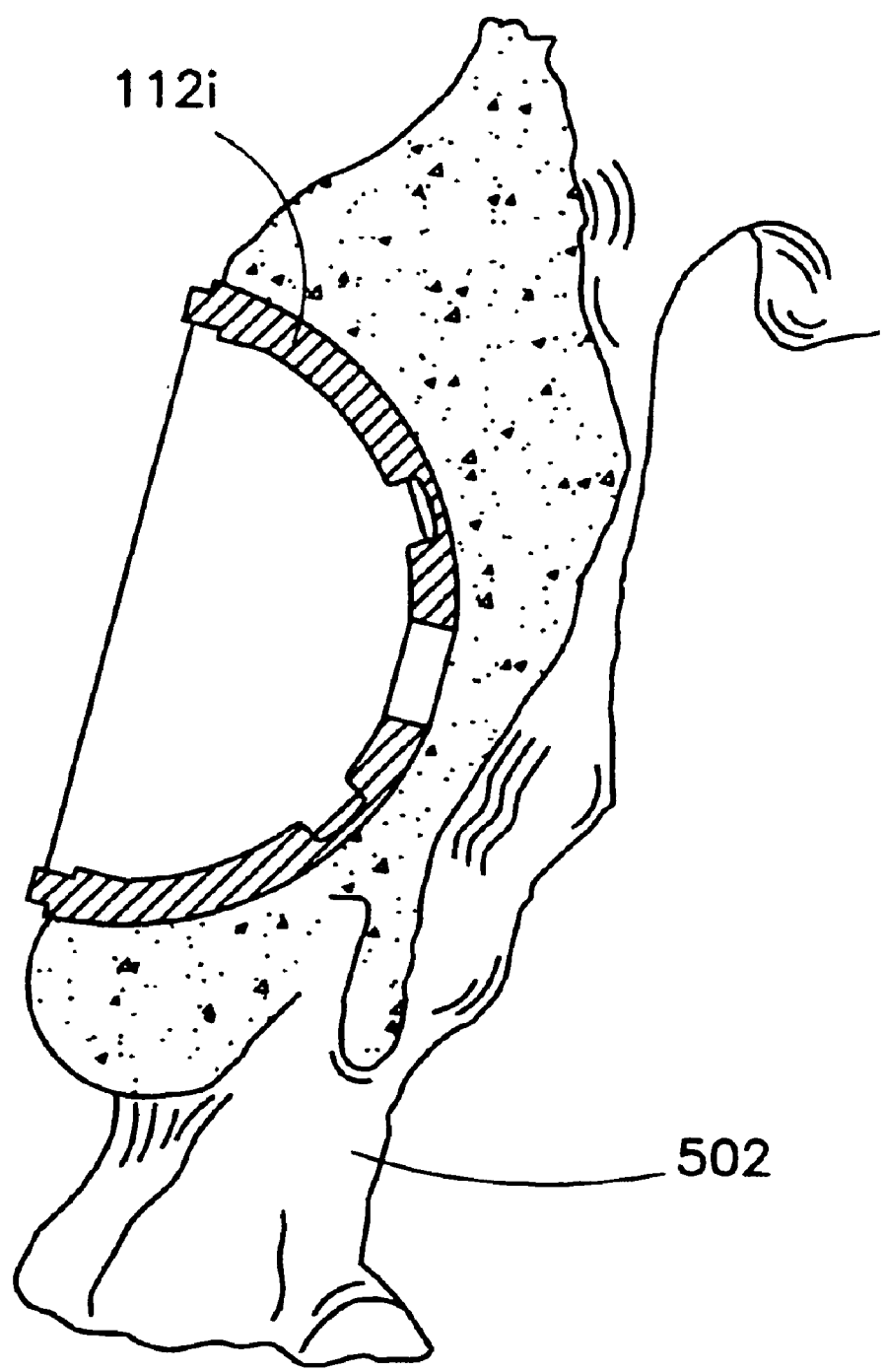
Figure 5C:
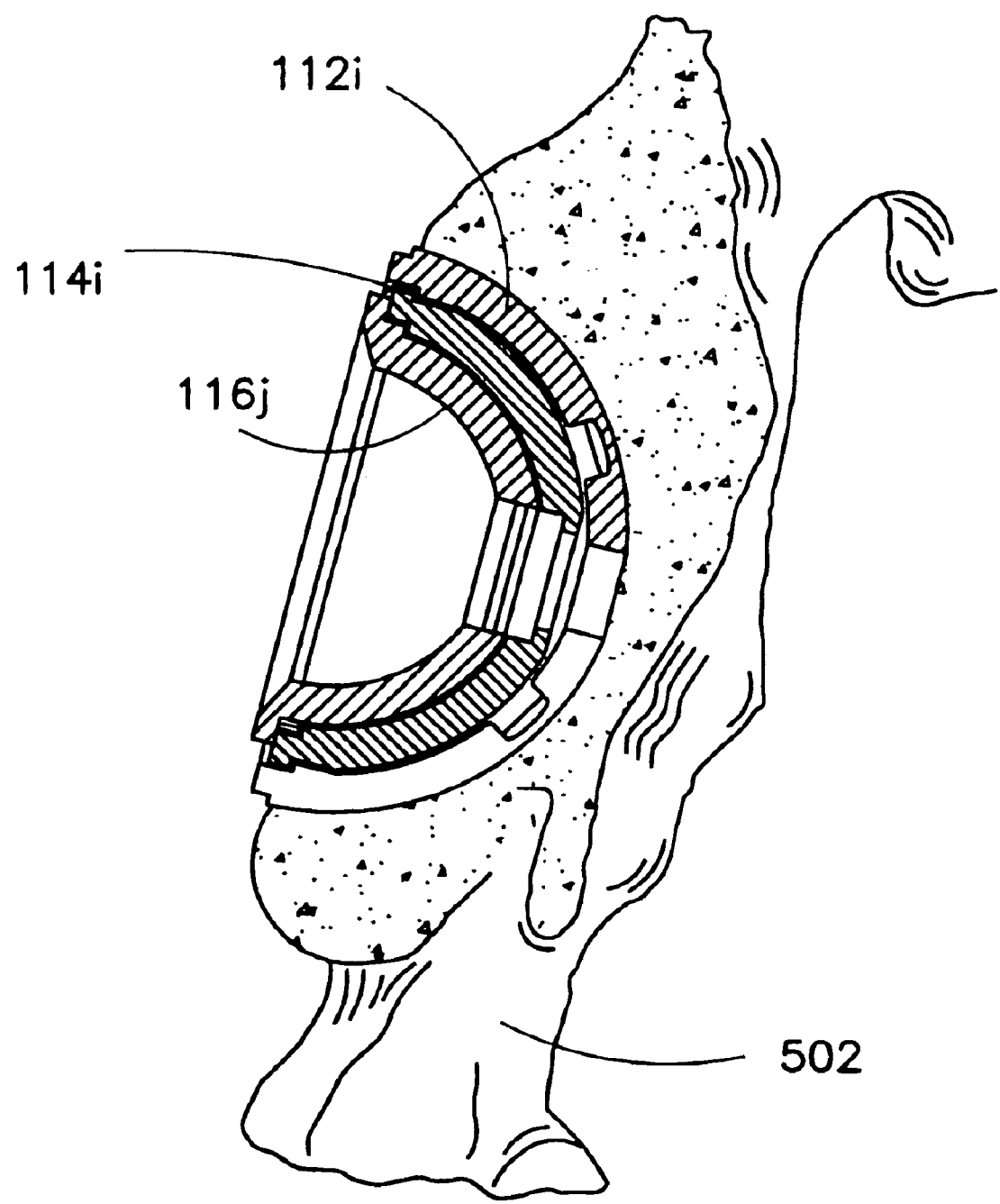

In practice, the acetabular trial kit 100 of the present invention may be used in either a total or partial hip replacement procedure in order to provide an artificial bearing surface. FIGS. 5a, 5b and 5c illustrate a surgical method for implanting an exemplary set of components from the kit 100 of FIG. 2.

Referring to FIG. 5a, a reamer, not shown, is used to ream or otherwise cut the acetabulum 502 in order to form a hemispherically shaped cavity 504 therein. The surgeon may then implant the trial outer shell 112i into the cavity 504, as illustrated by FIG. 5b. The outer shell 112i may be press fit or cemented into the cavity 504. The trial outer shell 112i is chosen based on the diameter of the cavity 504.

In a typical embodiment, the outer shell 112i is implanted into the cavity 504 separately and then the intermediate component 114i is secured to the outer shell 112i in vivo. The intermediate component 114i is chosen based on the selection of the trial outer shell 112i. For example, as shown in FIG. 2, each outer shell 112i has a corresponding intermediate component 114i with which it is used.

Thereafter, the surgeon selects a first trial inner component 116j. The surgeon secures the first trial inner component 116j to the intermediate component 114i and both devices are affixed to the outer shell 112i in vivo as shown in FIG. 5c. The first trial inner component 116j may suitably be affixed to the intermediate component 114i external to the body and then both devices are affixed to the outer shell 112i as a unit. However, in alternative embodiments, the intermediate component 114i alone may be affixed to the outer shell 112i in vivo, and then the trial component 116j would be affixed to the intermediate component 114i in vivo.

The surgeon then performs a trial reduction. To perform the trial reduction, the femoral head, not shown, is inserted into the cavity defined by the inner surface of the first trial inner component 116j. If the trial reduction is successful, the trial components may be removed and replaced with final implant components.

If, however, the trial reduction indicates a poor fit, poor alignment, or poor range of motion, then the first trial inner component 116j is removed from the intermediate component 114i and is replaced with a second trial inner component 116k which has a different configuration. For example, if the trial reduction indicated a poor fit, then the second trial inner component 116k may be selected such that is has a different size ID. If instead the trial reduction indicated poor alignment or poor range of motion but a good fit, then the second trial inner component 116k may be selected such that it has a different style, but the same ID. Once the second trial inner component 116k is secured within the intermediate component 114i, then another trial reduction is performed.

The replacement of the inner component may be repeated until the best combination of fit, alignment, and range of motion is achieved. During the trial reduction, the surgeon tests the alignment of the femur and range of motion. Suitable test methods are known in the art.

Once the appropriate inner component configuration is determined, corresponding final components may be implanted. In a preferred mode, the final outer shell, not shown, as a geometry substantially similar to the outer shell 112i, and the final inner liner, not shown, has a geometry that includes the outer diameter geometry of the intermediate component 114i and the inner diameter geometry of the trial inner liner component 116k.

It will be appreciated that the above describe embodiments are merely exemplary, and that those of ordinary skill in the art may readily devise their own implementations and variations that incorporate the principles of the present invention and fall within the spirit and scope thereof.

For example, the broader concepts of the invention described herein would provide at least some benefits in other types of orthopaedic implant systems, such as knees, shoulders or the like. In such devices, the components do not necessarily define substantially hemispherical shapes.

We claim:

1. An orthopaedic implant kit comprising:
   a plurality of outer shell components, each of at least two of the plurality of outer shell components having (i) an outer diameter that is distinct in size in relation to the outer diameter of the other of the at least two of the plurality of outer shell components, and (ii) an inner diameter that is distinct in size in relation to the inner diameter of the other of the at least two of the plurality of outer shell components;
   a plurality of intermediate components, each of at least two of the plurality of intermediate components having (i) an outer diameter that is distinct in size in relation to the outer diameter of the other of the at least two of the plurality of intermediate components, and (ii) an inner diameter that is uniform in size in relation to the Inner diameter of the other of the at least two of the plurality of intermediate components; and
   a plurality of bearing components, each of at least two of the plurality of bearing components having (i) an outer diameter that is uniform in size in relation to the outer diameter of the other of the at least two of the plurality of bearing components, and (ii) an inner diameter that is distinct in size in relation to the inner diameter of the other of the at least two of the plurality of bearing components.

2. The orthopaedic implant kit of claim 1, wherein each of the plurality of outer shell components has an outer surface configured to engage bone tissue.

3. The orthopaedic implant kit of claim 2, wherein said bone tissue is bone tissue of an acetabulum.

4. The orthopaedic implant kit of claim 1, wherein each of the plurality of bearing components has an inner surface configured to mate with a complementary configured bearing member.

5. The orthopaedic implant kit of claim 4, wherein said complementary configured bearing member is a bearing member of a femoral head.

6. The orthopaedic implant kit of claim 4, wherein the at least two of the plurality of outer shell components have uniform average wall thicknesses in relation to each other.

7. The orthopaedic implant kit of claim 6, wherein:
   the at least two of the plurality of intermediate components have distinct average wall thicknesses in relation to each other, and the at least two of the plurality of bearing components have distinct average wall thicknesses in relation to each other.

8. The orthopaedic implant kit of claim 1, further comprising a rotatable fastener configured to couple one of the plurality of intermediate components to one of the plurality of outer shell components.

9. A method of implanting an acetabular prosthesis, comprising:

providing a kit having:

a plurality of outer shell components, each of at least two of the plurality of outer shell components having (i) an outer diameter that is distinct in size in relation to the outer diameter of the other of the at least two of the plurality of outer shell components, and (ii) an inner diameter that is distinct in size in relation to the inner diameter of the other of the at least two of the plurality of outer shell components;

a plurality of intermediate components, each of at least two of the plurality of intermediate components having (i) an outer diameter that is distinct in size in relation to the outer diameter of the other of the at least two of the plurality of intermediate components, and (ii) an inner diameter that is uniform in size in relation to the inner diameter of the other of the at least two of the plurality of intermediate components; and a plurality of bearing components, each of at least two of the plurality of bearing components having (i) an outer diameter that is uniform in size in relation to the outer diameter of the other of the at least two of the plurality of bearing components, and (ii) an inner diameter that is distinct in size in relation to the inner diameter of the other of the at least two of the plurality of bearing components;

disposing one of the plurality of intermediate components of the kit within a first cavity of one of the plurality of outer shell components of the kit; and disposing one of the plurality of bearing components of the kit within a second cavity of the one of the plurality of intermediate components of the kit.

10. The method of claim 9, further comprising implanting the one of the plurality of outer shell components of the kit in the acetabulum of a patient.

11. The method of claim 9, wherein each of the plurality of bearing components of the kit has an inner surface configured to mate with a complementary configured bearing member of a femoral head.

12. The method of claim 9, further comprising:

coupling the one of the plurality of intermediate components of the kit to the one of the plurality of outer shell components of the kit with a rotatable fastener.

13. The method of claim 9, wherein the at least two of the plurality of outer shell components of the kit have uniform average wall thicknesses in relation to each other.

14. The method of claim 13, wherein:

the at least two of the plurality of intermediate components of the kit have distinct average wall thicknesses in relation to each other, and the at least two of the plurality of bearing components of the kit have distinct average wall thicknesses in relation to each other.

* * * * *